United States Patent [19]
Kim et al.

[11] Patent Number: 5,606,626
[45] Date of Patent: Feb. 25, 1997

[54] SPEAKER SYSTEM WITH AN ANION GENERATOR AND TELEVISION USING THE SPEAKER SYSTEM

[75] Inventors: Chan H. Kim, Daeku; Deog J. Lee, Kyungsangbook-do; Kyong S. Hwang, Daeku, all of Rep. of Korea

[73] Assignee: Goldstar Co., Ltd., Seoul, Rep. of Korea

[21] Appl. No.: 437,836

[22] Filed: May 16, 1995

Related U.S. Application Data

[63] Continuation of Ser. No. 192,816, Feb. 7, 1994, abandoned.

[30] Foreign Application Priority Data

Dec. 21, 1993 [KR] Rep. of Korea .................. 1993/28796
Jan. 28, 1994 [KR] Rep. of Korea .................... 1994/1568

[51] Int. Cl.⁶ ............................. H04R 25/00; H04R 7/00; H05K 5/00
[52] U.S. Cl. ........................... 381/159; 381/153; 381/188; 181/156; 181/167
[58] Field of Search .................................... 381/159, 160, 381/85, 180, 188, 205; 181/156, 167

[56] References Cited

U.S. PATENT DOCUMENTS

| | | | |
|---|---|---|---|
| 3,840,788 | 10/1974 | von Berckheim . | |
| 4,274,843 | 6/1981 | Sone et al. | 55/139 |
| 5,109,422 | 4/1992 | Furukawa | 381/159 |

FOREIGN PATENT DOCUMENTS

| | | | |
|---|---|---|---|
| 0492919 | 7/1992 | European Pat. Off. | 381/160 |
| 2423944 | 4/1978 | France . | |
| 2559981 | 2/1984 | France . | |
| 2452824 | 5/1976 | Germany . | |
| 2453235 | 5/1976 | Germany . | |
| 2509767 | 9/1976 | Germany . | |
| 0070394 | 3/1991 | Japan | 381/159 |

*Primary Examiner*—Sinh Tran

[57] ABSTRACT

A speaker system with an anion generator and a television set using the speaker system. The speaker system includes an anion generator provided within a speaker box. Sound pressure is used to help spread the generated anions outside the speaker box. An antistatic agent may optionally be provided on one or more surfaces of the speaker box to prevent static charge build-up within the speaker box.

26 Claims, 4 Drawing Sheets

SPEAKER SYSTEM WITH AN ANION GENERATOR AND TELEVISION USING THE SPEAKER SYSTEM

This application is a continuation of application Ser. No. 08/192,816 filed on Feb. 7, 1994, now abandoned.

BACKGROUND OF THE INVENTION

The present invention relates in general to a speaker system with an anion generator and a television set using the speaker system, and more particularly to a speaker system and a television set which spreads anions using sound generated by the speaker.

SUMMARY OF THE INVENTION

Conventionally, when watching a program from a television set or a video cassette tape recorder and listening to an audio output thereof in an area where many people are crowded, or some persons are gathered, the watchers or listeners could not be free from various harmful elements such as dust, polluted air from people smoking, etc.

Therefore, it is an object of the present invention to provide a speaker system with an anion generating function and a television set using the speaker system in which anions are generated to offer people a better environment while watching a television or video cassette tape recorder program or while enjoying music from an audio system in an environment free from the above-mentioned harmful problems.

Therefore, the present invention provides a television set with a speaker system having a means for generating anions so people can live in a better environment. The anions are obtained by an anion generator provided in the television set speaker system so as to be widely spread by the sound pressure of the speaker.

To achieve the above mentioned object of the invention, the speaker system of the present invention includes a speaker provided at a predetermined position in a speaker box, a sound output hole provided at a front face of said speaker box for outputting sound in the forward direction, a port provided at a lower portion of said sound output hole for outputting rearwardly generated sound within the speaker box to the forward direction, and an anion generator located so that sound from the speaker spreads the anions.

In another aspect of the present invention, a television set having a cabinet includes: a speaker box with speaker; a sound outputting hole provided at a predetermined position of a front face of said speaker box for outputting sound in the forward direction; a port for outputting sound within the speaker box, and an anion generator positioned so that generated anions are spread by sound from the speaker.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE PREFERRED EMBODIMENTS

Figure 1:
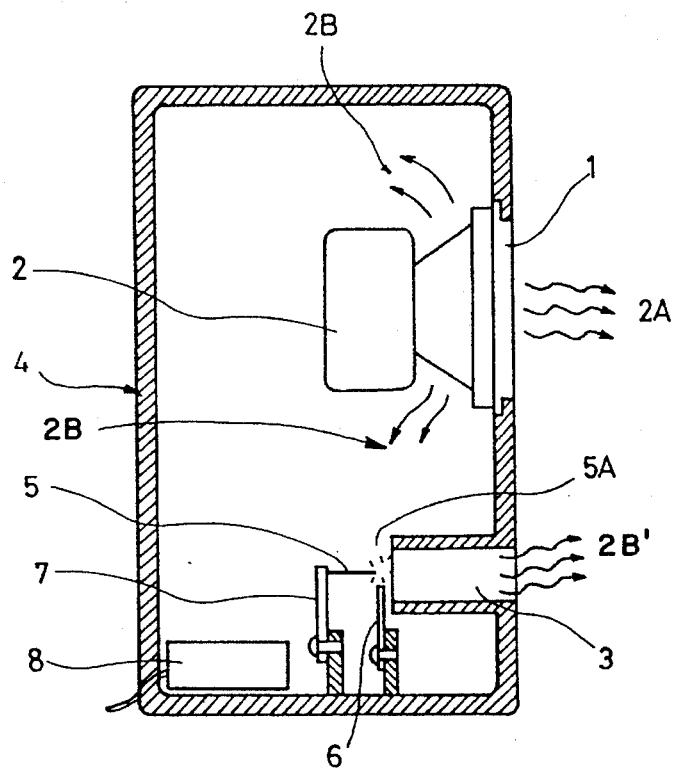
FIG. 1 is a sectional view illustrating a first embodiment of the invention.

Referring to FIG. 1, there is illustrated a sectional view of the first embodiment of the invention. As illustrated in this drawing, a speaker system with anion generator includes a speaker box 4 having a sound outputting hole 1 for outputting forwardly generated sound 2A from the speaker 2 and a port 3, provided at lower part of the sound outputting hole 1, for outputting a portion 2B' of the rearwardly directed sound 2B within the speaker box 4 to the forward direction. A discharge needle 5 for generating anions and a confronting electrode 6 for helping the discharging process are provided at a position nearby the port 3 of the speaker box. Also, a printed circuit board 7 to which the discharge needle is fixed and a high voltage generator 8 for applying high voltage to the discharge needle 5 through the circuit board 7 are provided.

The anions generating and spreading process according to the first embodiment of the invention will now be described.

When an audio system or a VTR is energized, the speaker 2 vibrates in response to the audio input to the speaker. As a result of the vibration of the speaker 2, forwardly generated sound 2A is provided through the sound outputting hole 1 and the sound 2B' is provided through the port 3 through the inside space of the speaker box 4.

When electric power is applied to the high voltage generator 8, the high voltage generator 8 applies the produced high voltage to the discharge needle 5 fixed to the circuit board 7. The discharge needle 5 discharges to the confronting electrode 6 and generates anions(5A) as a result of this process. The anion-generation process can be represented as follows:

The confronting electrode 6 helps the discharging process of the discharge needle 5 to generate many anions(5A).

Figure 2:
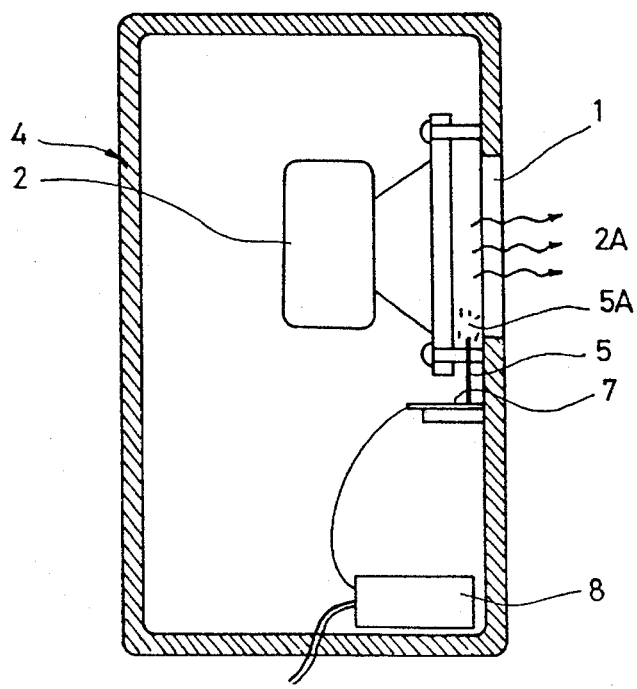
FIG. 2 is a sectional view illustrating a second embodiment of the invention.

Referring to FIG. 2, the second embodiment of the invention comprises: a speaker box 4 in which there is a sound outputting hole 1 for outputting the forwardly generated sound 2A to the forward direction of the speaker 2, a discharge needle 5 located between the speaker 2 and the sound outputting hole for generating the anions; a circuit board 7 in which the discharge needle 5 is fixed thereon; and a high voltage generator 8 for applying the produced high voltage to the discharge needle 5 through the circuit board 7.

In the second embodiment, there is not provided a confronting electrode, but if a higher output is needed, a confronting electrode may optionally be provided.

The spreading process of the anions according to the second embodiment of the invention will now be described.

When an audio or VTR machine is energized, the speaker 2 vibrates in response to the audio input and, as a result of the vibration, the forwardly generated sound 2A is provided through the sound outputting hole 1 to the forward direction.

When electric power is applied to the high voltage generator 8, the high voltage generator 8 applies the produced high voltage to the discharge needle 5 fixed at the circuit board 7. The anions generated by this process are spread by means of the sound pressure of the forwardly generated sound 2A of the speaker 2 through the sound outputting hole 1, whereby anions are spread into the indoor space in which this system is located.

This process will go on by means of the sound pressure of the forwardly generated sound 2A with the vibration of the speaker 2; thus, an indoor space in which this system may be located will be provided with anions. A confronting electrode (not shown) may optionally be provided to help the discharging process of the discharge needle 5 to generate anions (5A)).

Figure 3:
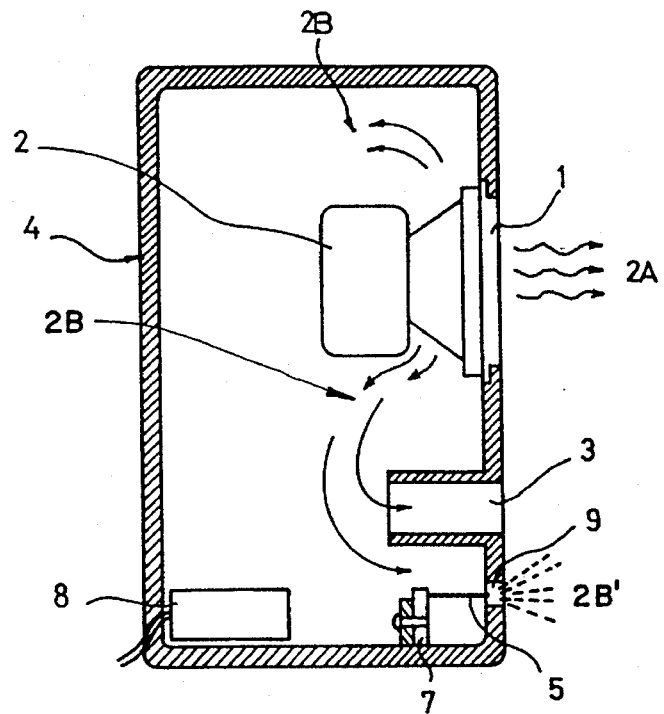
FIG. 3 is a sectional view illustrating a third embodiment of the invention.

Referring to FIG. 3, the third embodiment of the invention comprises a speaker box 4 including a sound outputting hole 1 outputting the forwardly generated sound 2A to the forward direction of the speaker 2, and a port 3, provided at lower portion of the sound outputting hole 1, for outputting a portion 2B' of the rearwardly generated sound 2B within the speaker box 4 to the forward direction. There is further provided an anions discharging port 9 located a predetermined position of the speaker box, a discharge needle 5 provided near to or inside the anions discharging hole 9 for generating anions, a circuit board which supports the discharge needle 5, and a high voltage generator 8 for applying high voltage to the discharge needle 5 through the circuit board 7.

The anions generating and spreading process according to the third embodiment of the present invention now will be described.

When an audio or VTR machine is energized, the speaker 2 vibrates in response to the audio input and, as a result of the vibration, the forwardly generated sound 2A is provided through the sound outputting hole 1 to the forward direction and a portion 2B' of the rearwardly generated sound 2B is provided to the port 3.

When electric power is applied to the high voltage generator 8, the high voltage generator 8 applies the produced high voltage to the discharge needle 5 fixed at the circuit board 7. The anions generated by this process are spread by means of the sound pressure of the sound 2B of the speaker 2 through the sound outputting hole 1, whereby the anions are spread into the indoor space in which this system is located.

Figure 4A:
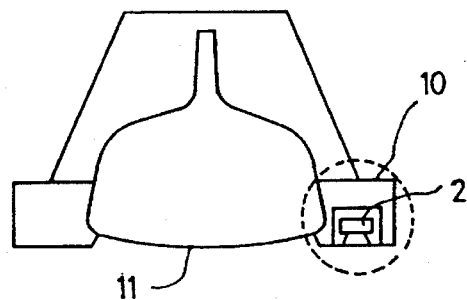
FIGS. 4A and 4B are schematic views illustrating a television cabinet with a speaker box therein.
Figure 4B:
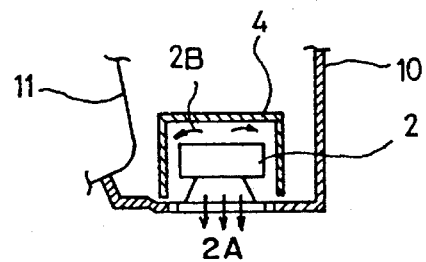

FIGS. 4A and 4B illustrate a speaker 2 provided in the cabinet 10 of the television set, with the anions generating means positioned in the speaker box 4 according to the first embodiment of the present invention.

Thus, electric power is applied to the television set, sound is outputted from speaker 2, and anions are spread into the indoor space by means of the rewardly generated sound 2B.

In the drawings, reference numeral 11 denotes a CRT, and the discharge needle 5 may be provided at a predetermined position inside the cabinet 10, assuming the entire portion of the television cabinet 10 is the speaker box.

Figure 5:
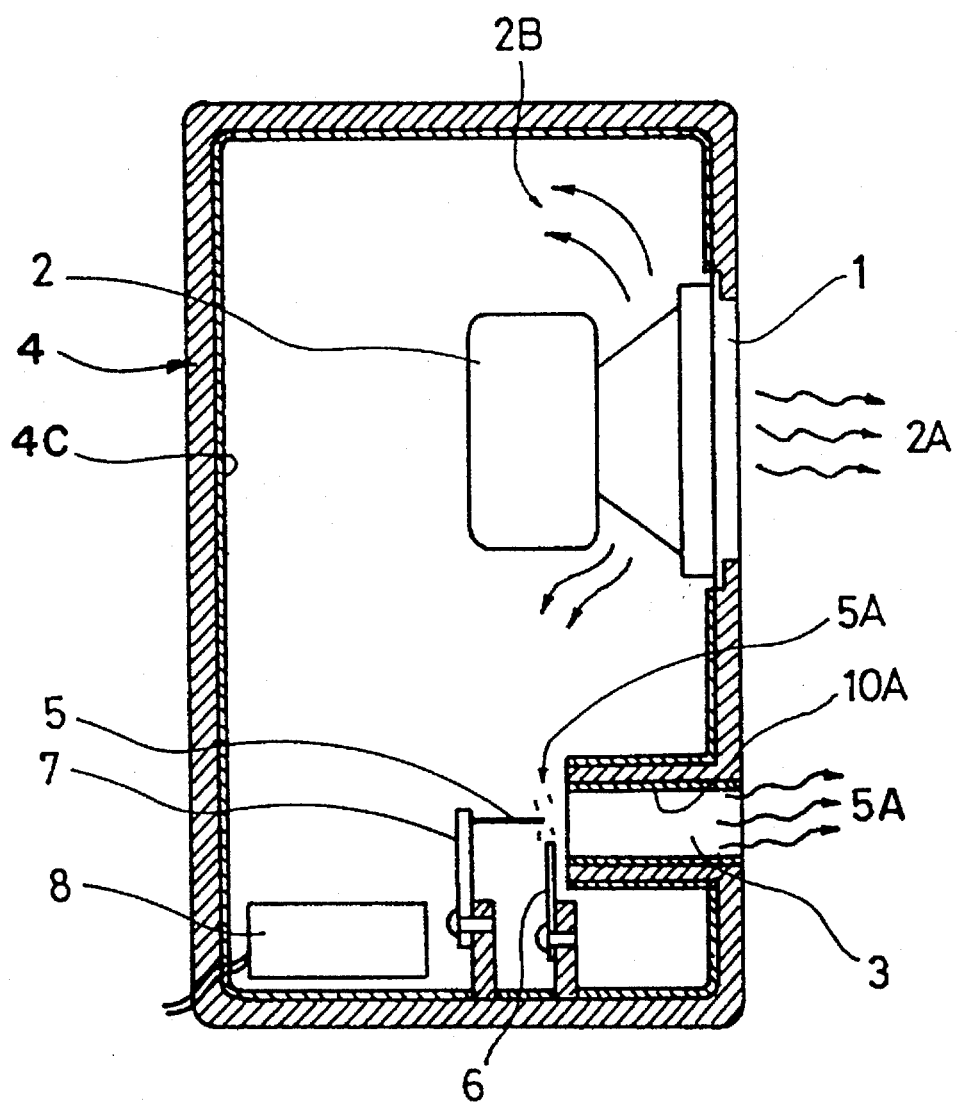
FIG. 5 is a sectional view illustrating a fourth embodiment of the invention.

FIG. 5 is a view illustrating a fourth embodiment of the invention. This embodiment is identical to the first embodiment and will not be described except to note that there is additionally provided a anti-static coating 4C on the inside wall of the speaker box 10 for preventing static charge build-up from being formed on the inside wall of the speaker box 10 by the discharge.

Because the electrons (e−) generated according to the anions generation process reach the inner surface of the cabinet 4 faster than the ions $O_2$, (the electrons (e−) move faster than ions $O_2$) there is provided an antistatic agent coated on an inside surface of the cabinet.

In addition, to the embodiments illustrated it may be possible to coat the antistatic agent (10A) on the surface of the port 3. In this case, since the antistatic agent (10A) is also coated on the surface of the anions discharging port 3, static charge on the port 3 is eliminated, thus the anions generated as described above can be spread into the indoor space while freely passing through the port 3. U.V. materials may be provided on the inner surface of the cabinet 10 to prevent static charge build-up since the electrons (e−) of the U.V. materials are prevented from attaching to the inner surface of the cabinet 10. Also, static charge buildup can be prevented by combining an antistatic agent into the plastic materials to be moulded into the cabinet. In this case, static charge problems during anion formation can be prevented. Or, one could provide paper sheets or PVC sheets coated with U.V. materials thereon, in addition to antistatic agents. Finally, antistatic agents (4C) could be coated on the inner surface of the cabinet 4 and U.V. coating tape could be attached to the port 3. Alternatively, it is also possible to coat the antistatic agents (10A) on the port 3 and to provide U.V. coating tape on the inner surface of the cabinet 10.

Figure 6:
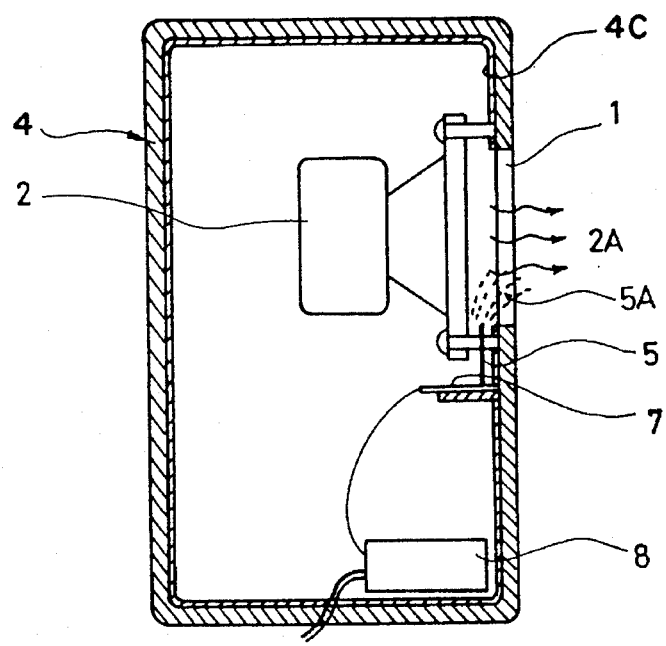
FIG. 6 is a sectional view illustrating a fifth embodiment of the invention.

FIG. 6 illustrates the fifth embodiment of the invention.

This embodiment is similar to the second embodiment shown in FIG. 2 except that anti-static agents (4C) are coated on the inner surface of the cabinet 4.

The anions generating and spreading process according to the fifth embodiment is same as that of the second embodiment described hereinbefore, so further description thereof will not be provided.

It is possible to form the cabinet 10 including the antistatic agents (4C) as illustrated in FIG. 5 wherein U.V. coating materials are used for the antistatic agents (4C), and U.V. coating tape is attached to the inner surface of the cabinet 10. In either case, the same effects as that described in the embodiment of FIG. 5 can be obtained.

Figure 7:
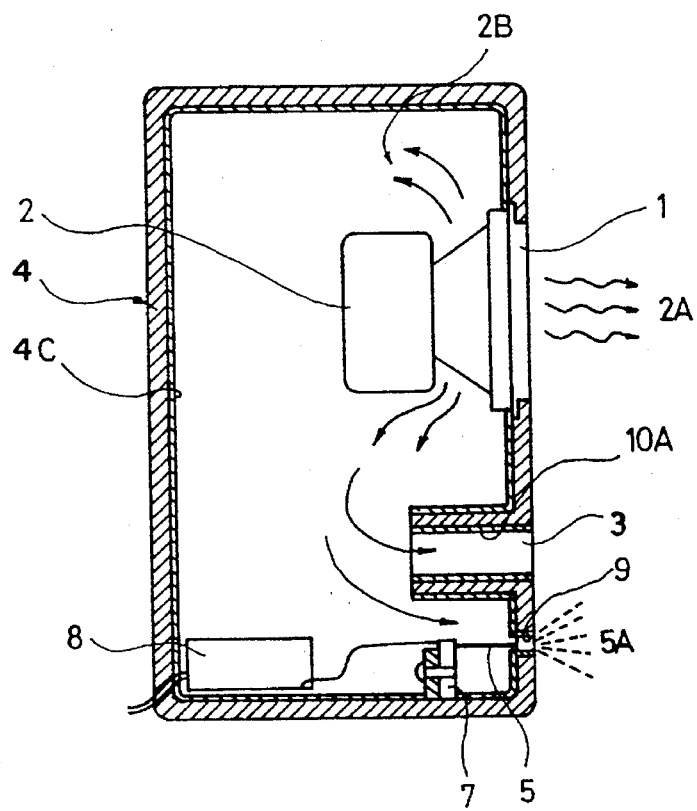
FIG. 7 is a sectional view illustrating a sixth embodiment of the invention.

FIG. 7 illustrates the sixth embodiment of the invention.

This embodiment is similar to the third embodiment shown in FIG. 3 except that antistatic agents (4C) and U.V. materials (10A) for preventing the formation of static charge are respectively provided on the inner wall of the sound outputting port 3 and on the inner wall of the anions discharging hole 5A.

The invention permits anions to be generated and dispersed while watching a television program. Since static charge is avoided, anions can be generated and effectively spread by means of the sound pressure of a speaker system.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A speaker system with an anion generator, comprising:
a speaker provided at a predetermined position in a speaker box;

a sound output hole, provided at a front face of said speaker box, for outputting forwardly generated sound from the speaker to a forward direction;

a port, provided below said sound output hole, for outputting rearwardly generated sound from the speaker within said speaker box to the forward direction; and anions generating means for generating anions such that sound pressure of the rearwardly generated sound from the speaker spreads said anions through said port.

2. The speaker system of claim 1, wherein said anions generating means includes a high voltage generator, a discharge needle energized by a high voltage at said high voltage generator, a circuit board for applying the high voltage generated at said high voltage generator to said discharge needle, and a confronting electrode for assisting the discharge needle to produce many anions.

3. The speaker system of claim 2, wherein said discharge needle is provided nearby the interior opening of said port.

4. The speaker system of claim 1, wherein said anions generating means includes a high voltage generator provided at one side of the bottom of said speaker box, a discharge needle, located nearby said port of said speaker box, for generating anions by being discharged by a high voltage supplied by said high voltage generator, a circuit board for applying the high voltage generated at said high voltage generator to said discharge needle, and a confronting electrode for assisting said discharge needle to produce many anions.

5. The speaker system of claim 1, wherein said anions generating means includes a high voltage generator, a discharge needle provided nearby an inside wall of the front face of said speaker box for generating anions, and a circuit board for applying the high voltage generated at said high voltage generator no said discharge needle.

6. A speaker system with an anion generator, comprising:
   a speaker provided at a predetermined position in a speaker box;
   a sound output hole, provided at a front face of said speaker box, for outputting forwardly generated sound from the speaker to a forward direction; and
   anions generating means for, generating anions within said speaker box such that the forwardly generated sound from said speaker spreads said anions;
   wherein said anions generating means includes a high voltage generator, a discharge needle for generating the anions by being discharged by a high voltage supplied by said high voltage generator, and a circuit board for applying the high voltage generated at said high voltage generator to said discharge needle, said discharge needle passing through a holder provided between said speaker and said sound output hole.

7. A speaker system with an anion generator, comprising:
   a speaker provided at a predetermined position in a speaker box;
   a sound output hole, provided at a front face of said speaker box, for outputting forwardly generated sound form the speaker to a forward direction;
   a port, provided below said sound output hole, for outputting rearwardly generated sound from the speaker within said speaker box to a forward direction; and
   anions generating means, including a high voltage generator, a discharge needle provided nearby an inside wall of the front face of said speaker box for generating anions, and a circuit board for applying a high voltage generated at said high voltage generator to said discharge needle;
   wherein said anions generating means further includes an anions discharging hole for discharging anions provided at a predetermined position at the front face of said speaker box, said anions being spread by the sound within said speaker box by positioning the discharge needle adjacent or inside said discharging hole.

8. The speaker system of claim 7, wherein said anions generating means includes a discharge needle disposed adjacent said discharging hole.

9. The speaker system of claim 7, wherein said discharging hole is coated with an antistatic agent.

10. The speaker system of claim 7, wherein ultraviolet material is coated on a wall of said anions discharging hole.

11. The speaker system of claim 10, wherein said ultraviolet material is coated on a sheet and attached on a wall of said discharging hole in a form of a tape.

12. In a television set having a cabinet with a speaker system, the improvement comprising:
   a speaker box with a speaker and provided at a predetermined position in said television set;
   a sound output hole provided at a predetermined position on a front face of said speaker box for outputting forwardly generated sound from the speaker in a forward direction;
   a port for outputting rearwardly generated sound from the speaker to said forward direction; and
   anions generating means for generating anions, said anion generating means positioned so that said anions are spread by said rearwardly generated sound from said speaker through said port.

13. The television set of claim 12, wherein said anion generating means includes a high voltage generator, a discharge needle provided adjacent a front face of said speaker box for generating anions, and a circuit board for applying a high voltage generated at said high voltage generator to said discharge needle.

14. The television set of claim 13, wherein said discharge needle is provided adjacent said front face of said speaker box.

15. The television set of claim 12, wherein said discharge needle is provided nearby an interior opening of said port.

16. The television set of claim 12, wherein said anions generating means includes a high voltage generator, a discharge needle provided nearby an inside wall of said front face of said speaker box for generating anions, and a circuit board for applying a high voltage generated at said high voltage generator to said discharge needle.

17. The television set of claim 12, further comprising:
   an antistatic agent for preventing static charge build-up within said speaker box.

18. The television set of claim 17, wherein said antistatic agent is coated on an inside surface of said speaker box.

19. The television set of claim 17, said port is coated with said antistatic agent.

20. The television set of claim 17, wherein said antistatic agent is integrally molded with said speaker box.

21. A television set of claim 12, further comprising:
   an ultraviolet material for preventing static charge build-up within said speaker box.

22. The television set of claim 21, wherein said ultraviolet material is coated on the inside wall of said speaker box.

23. The television set of claim 21, wherein sid ultraviolet material is coated in a form of a tape.

24. The television set of claim 21, wherein said ultraviolet material is coated on a wall of said output port.

25. The television set of claim 24, wherein said ultraviolet material is coated in a form of a tape.

26. In a television get having a cabinet with a speaker system, the improvement comprising:
   a speaker box with a speaker and provided at a predetermined position in said television set;
   a sound output hole provided at a predetermined position on a front face of said speaker box for outputting forwardly generated sound from the speaker in a forward direction; and anions generating means for generating anions, said means positioned so that said anions are spread by said for wardly generated sound from said speaker;

wherein said anion generating means includes a high voltage generator, a discharge needle provided adjacent a front face of said speaker box for generating anions, and a circuit board for applying a high voltage generated at said high voltage generator to said discharge need, said discharge needle passing through a holder provided between said front face of said speaker and said sound output hole.

* * * * *